(12) United States Patent
Hofeldt

(10) Patent No.: US 7,857,450 B1
(45) Date of Patent: Dec. 28, 2010

(54) HAND-HELD DEVICE FOR CONTRAST AND MULTIFUNCTION VISION TESTING

(76) Inventor: Albert John Hofeldt, 314 W. San Marino Dr., Miami Beach, FL (US) 33139

( * ) Notice: Subject to any disclaimer, the term of this patent is extended or adjusted under 35 U.S.C. 154(b) by 369 days.

(21) Appl. No.: 12/012,561

(22) Filed: Feb. 4, 2008

(51) Int. Cl.
*A61B 3/02* (2006.01)

(52) U.S. Cl. .................. 351/243; 351/233; 351/234; 351/239; 351/244

(58) Field of Classification Search .................. 351/208, 351/216, 217, 233, 234, 239, 243, 244
See application file for complete search history.

(56) References Cited

U.S. PATENT DOCUMENTS 5,398,085 A * 3/1995 Hofeldt ....................... 351/243

* cited by examiner

*Primary Examiner*—Jack Dinh

(57) ABSTRACT

A vision testing device for measuring single or multiple visual functions consisting of an internally illuminated hand-held instrument, vision charts, vision correcting and occluding elements, a testing frame for holding combined vision correcting and blocking elements, and modular accessories.

19 Claims, 14 Drawing Sheets

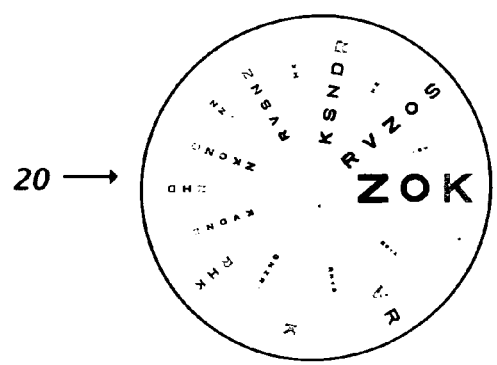
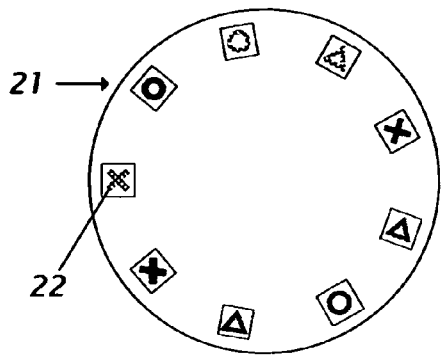
FIG. 2A  FIG. 2B
blue
red
green
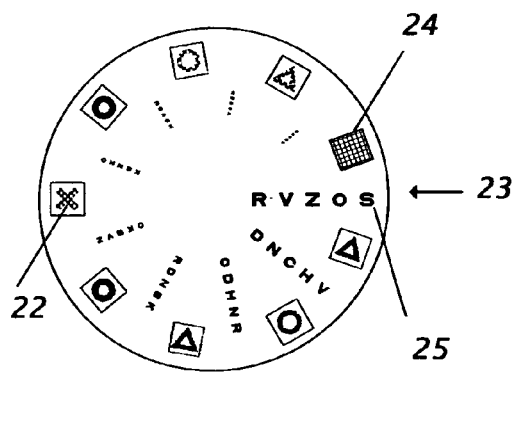
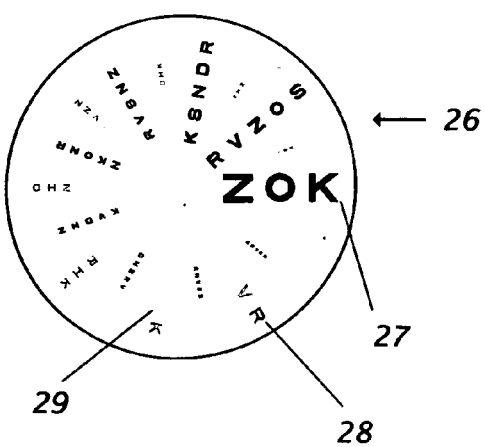
FIG. 2C  FIG. 2D

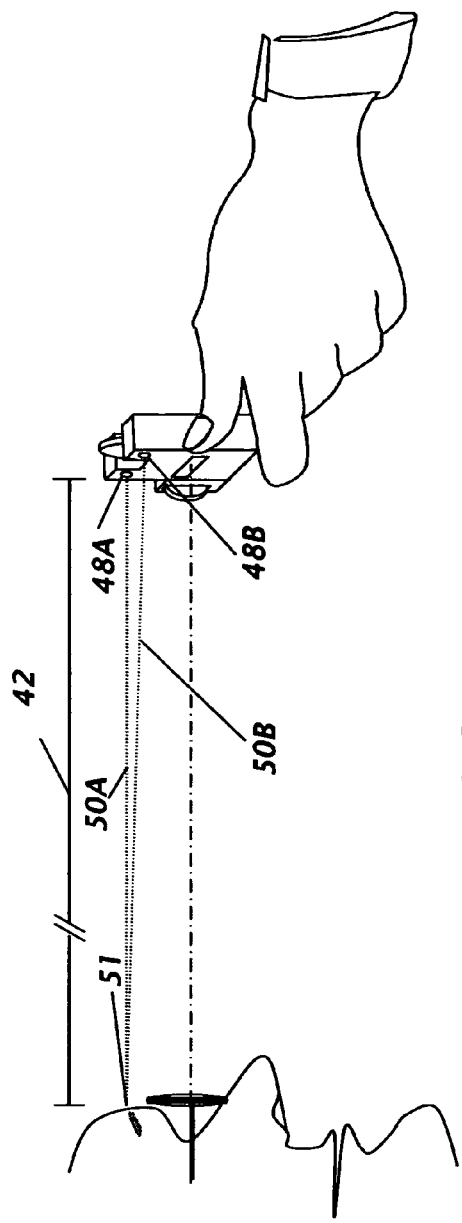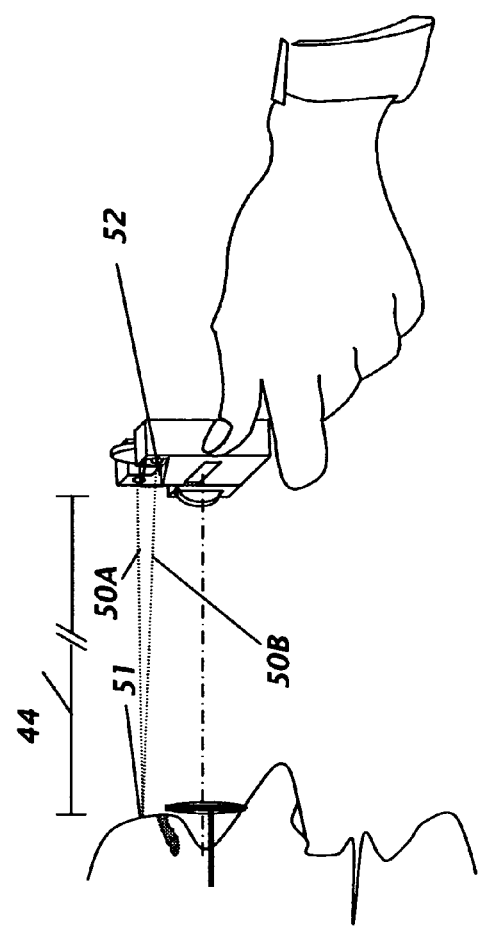

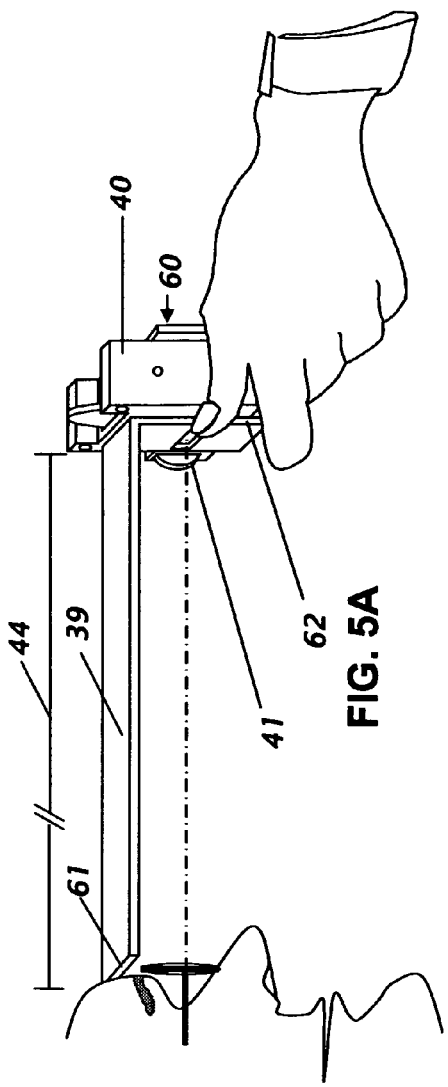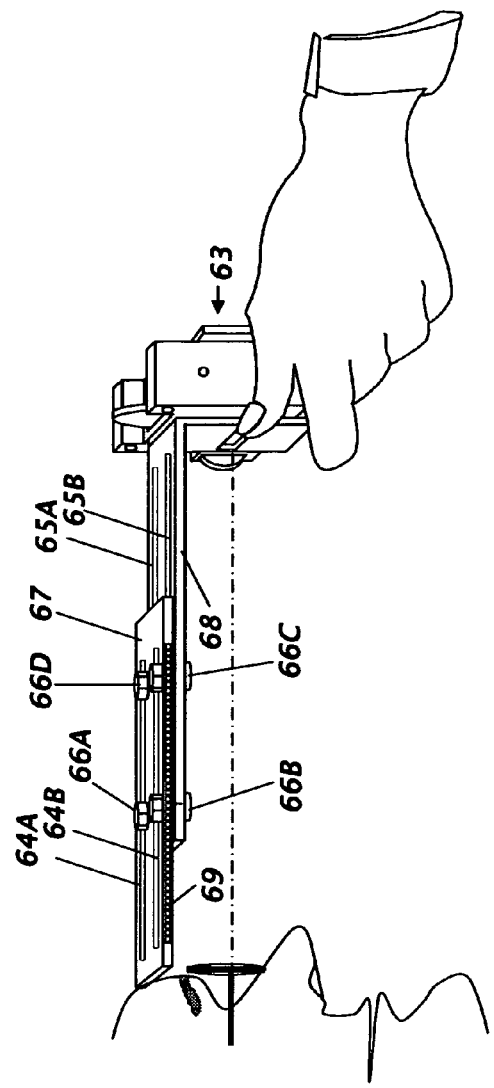
FIG. 5A
FIG. 5B

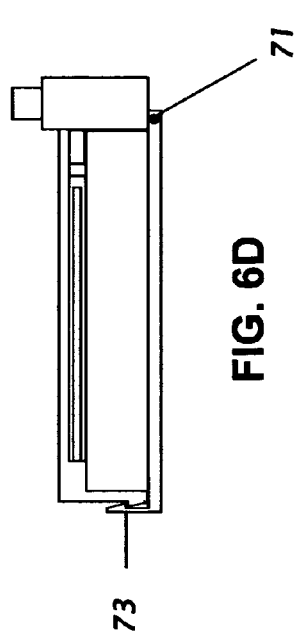
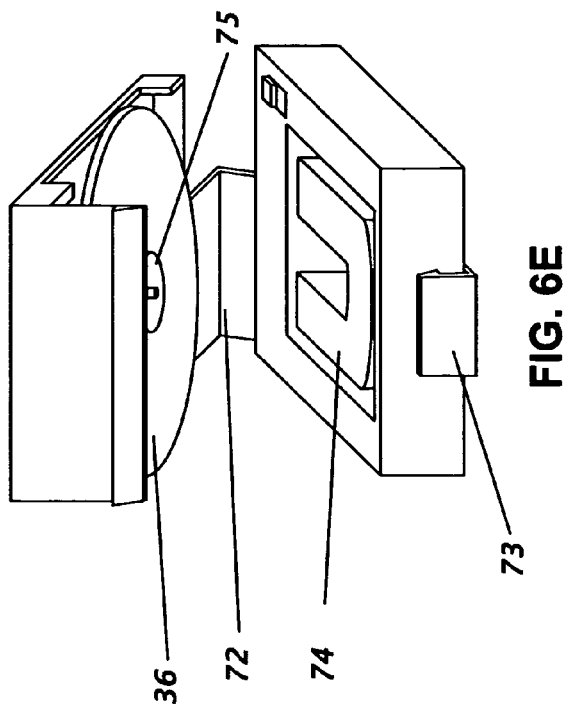
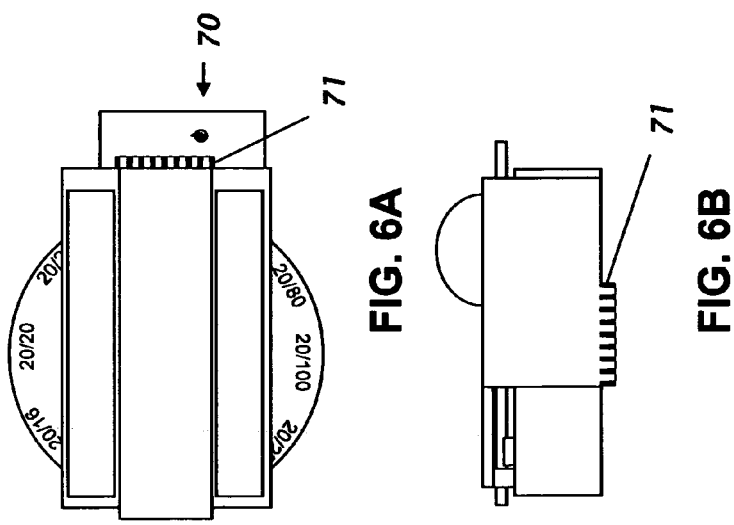
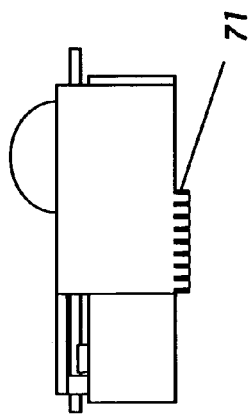
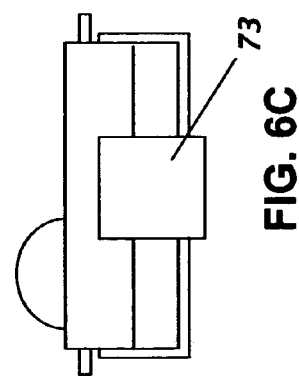

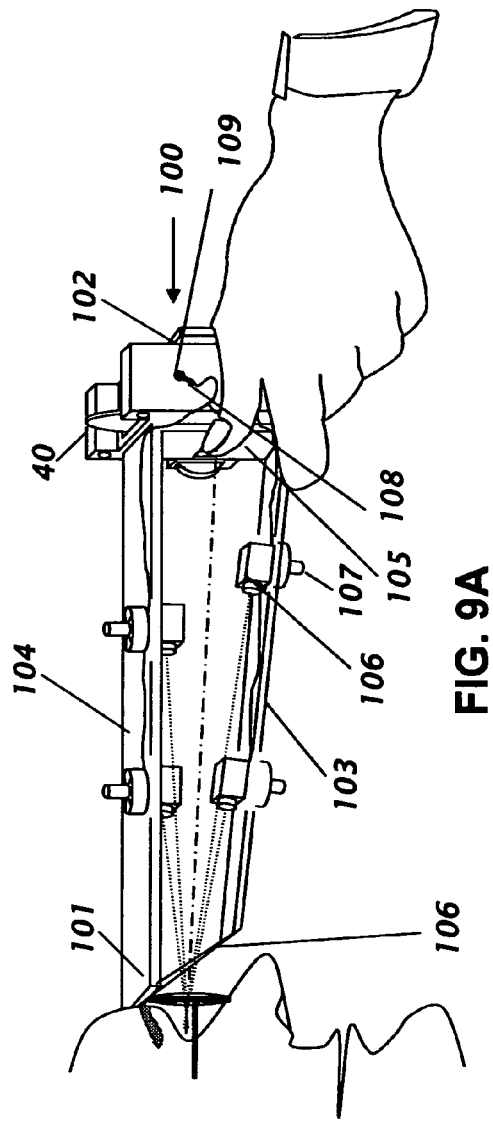
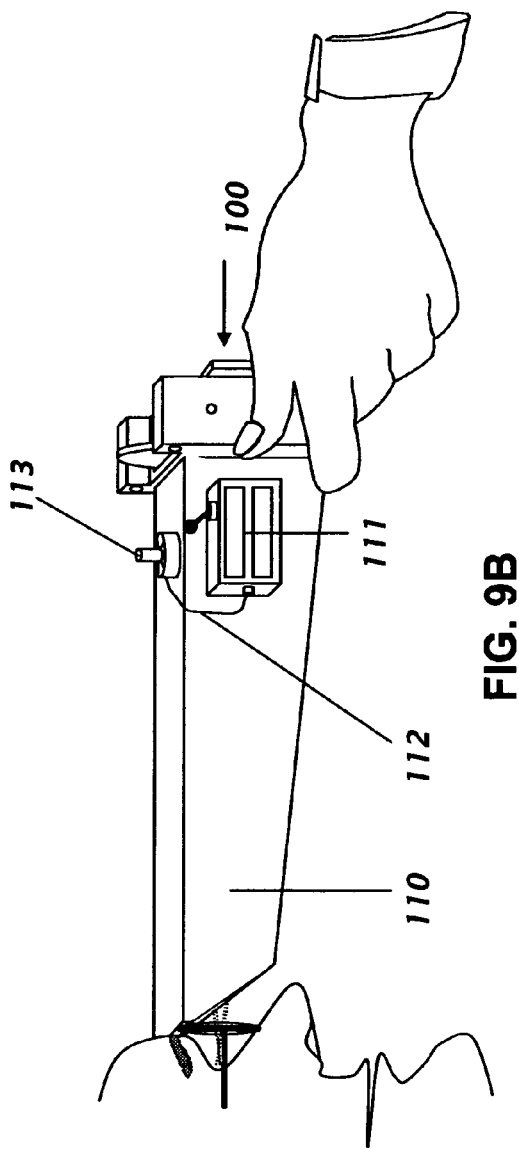
FIG. 9A
FIG. 9B

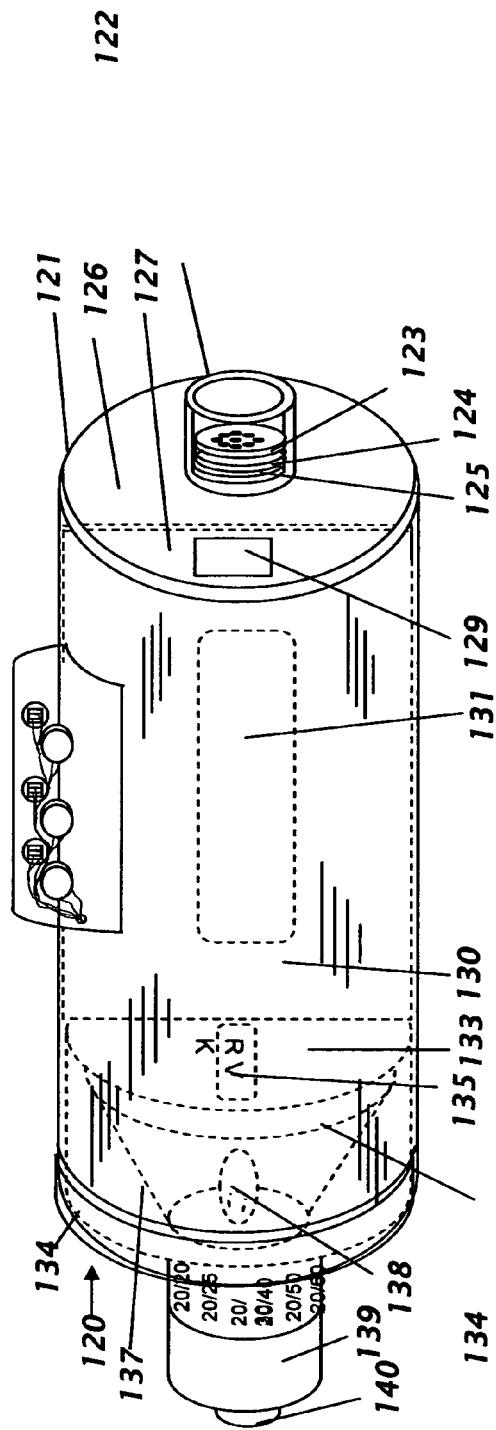
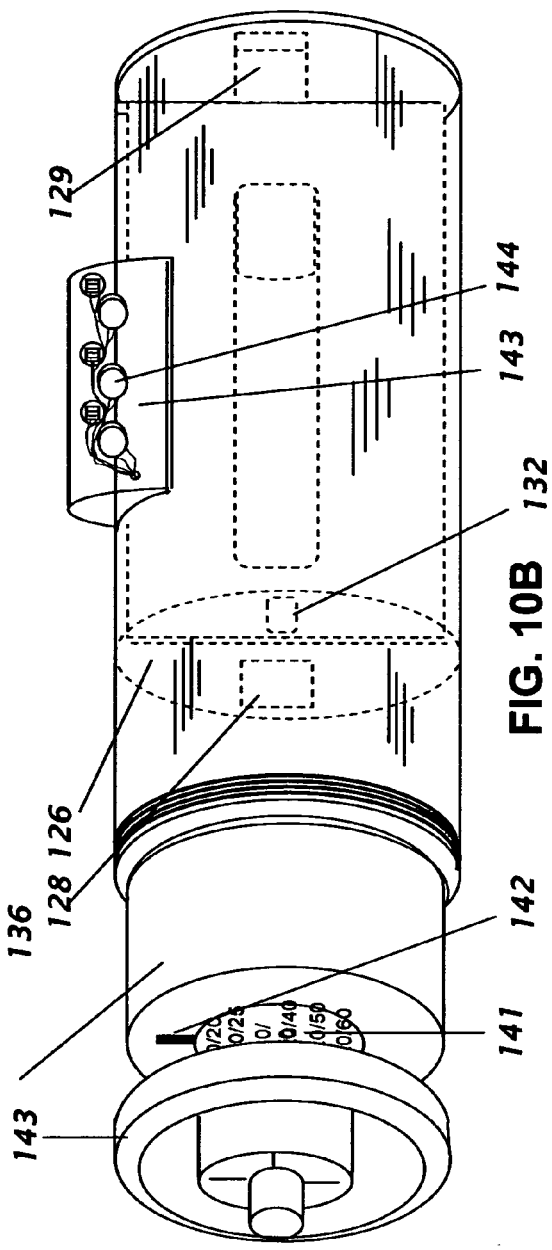
FIG. 10A
FIG. 10B

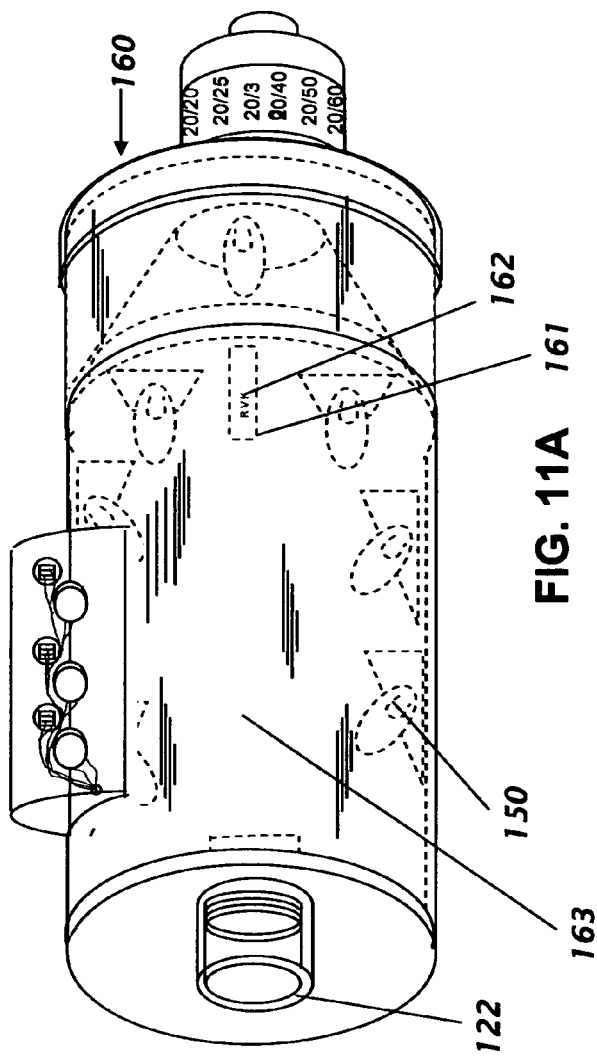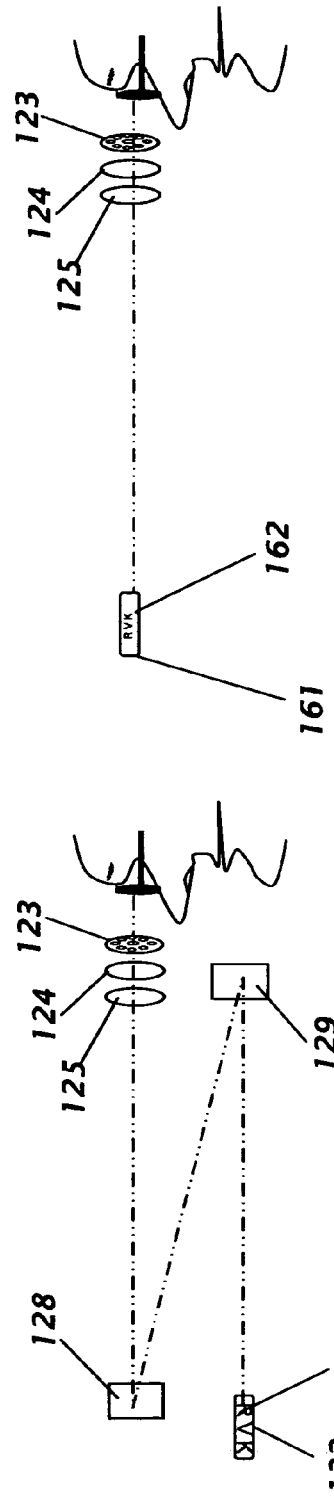

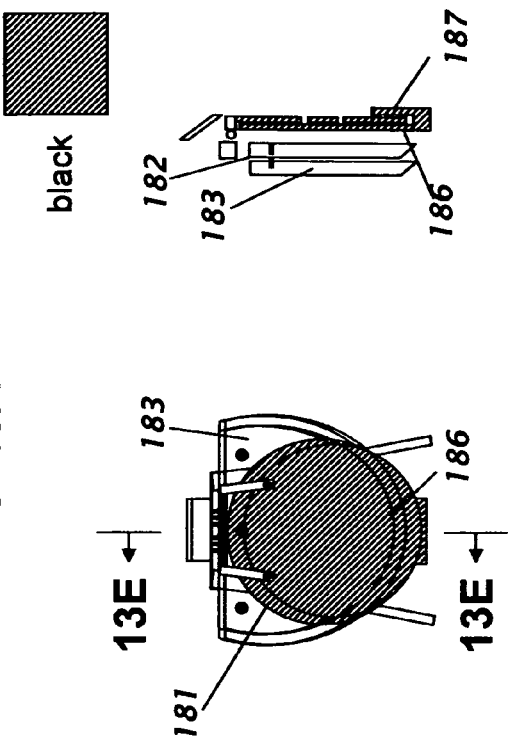 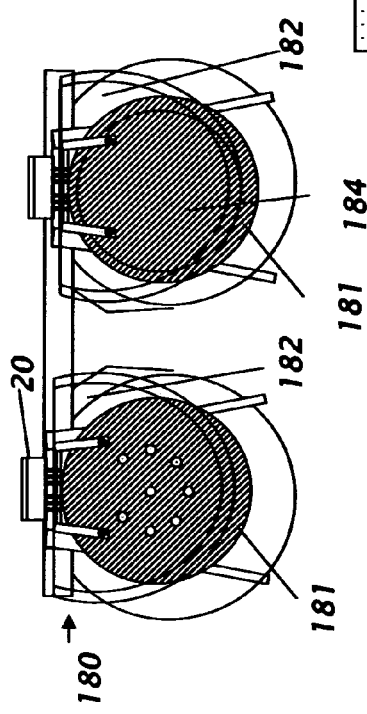 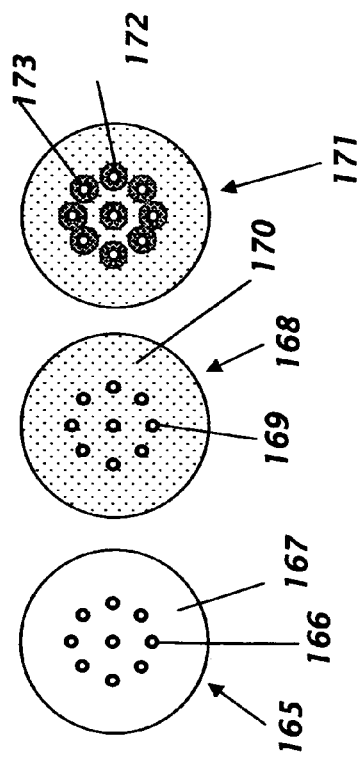 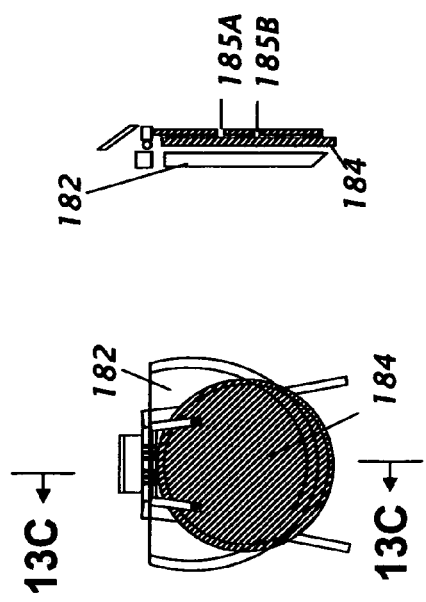

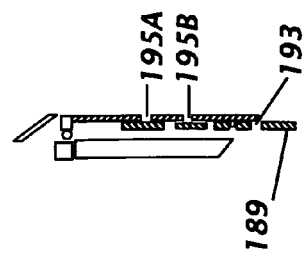
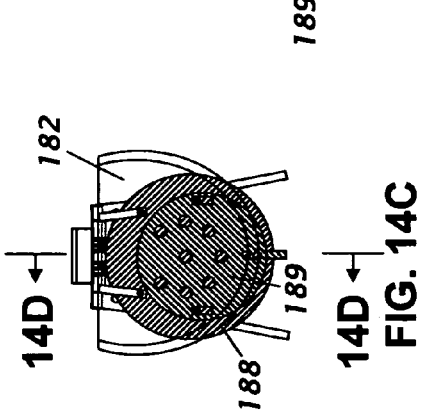
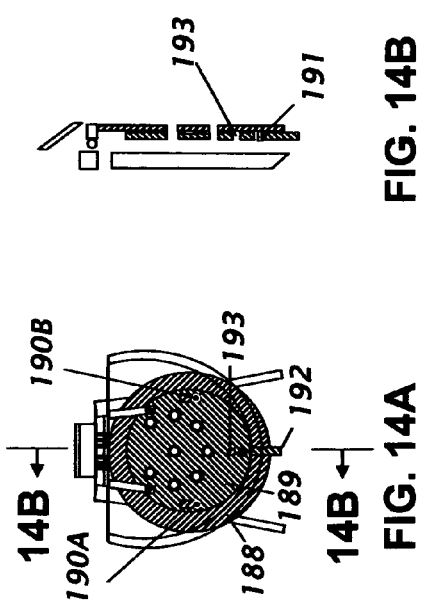
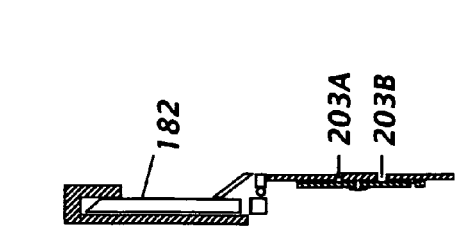
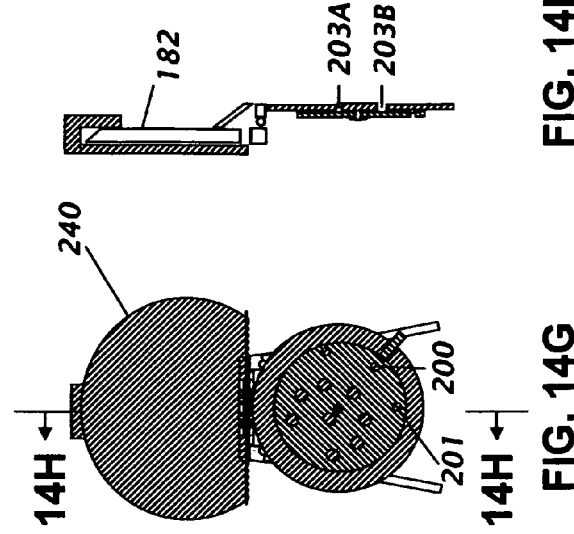
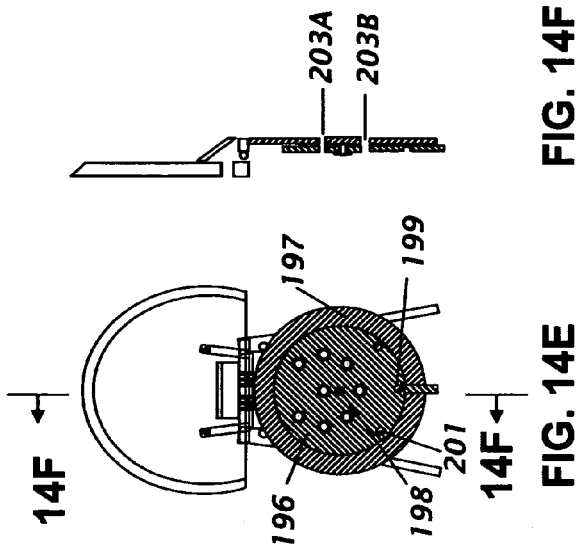

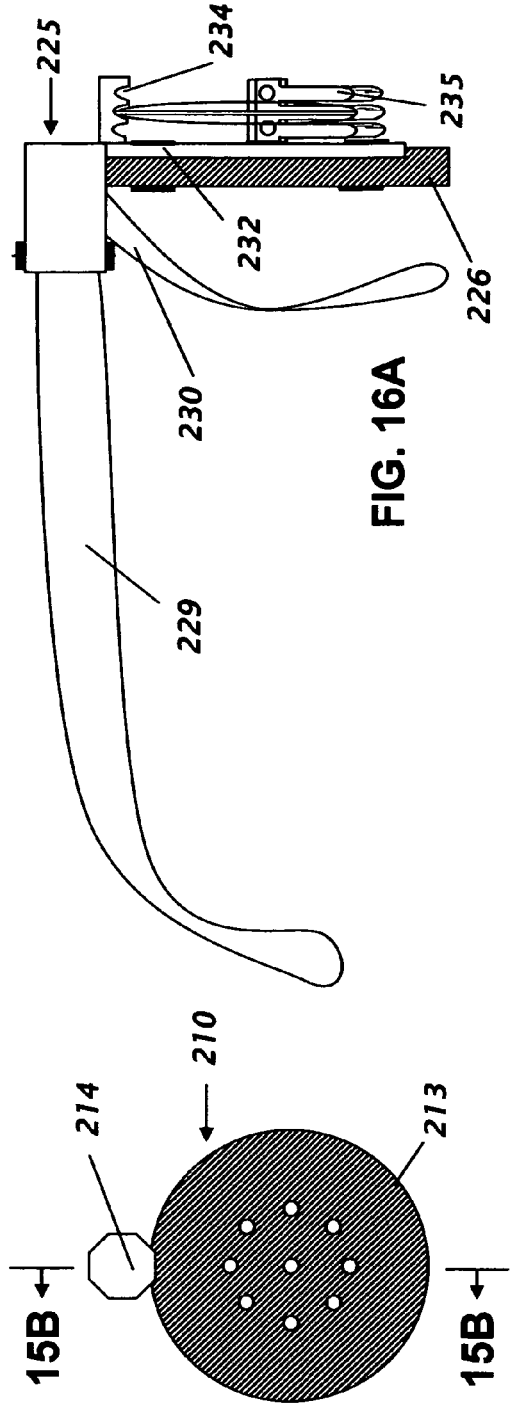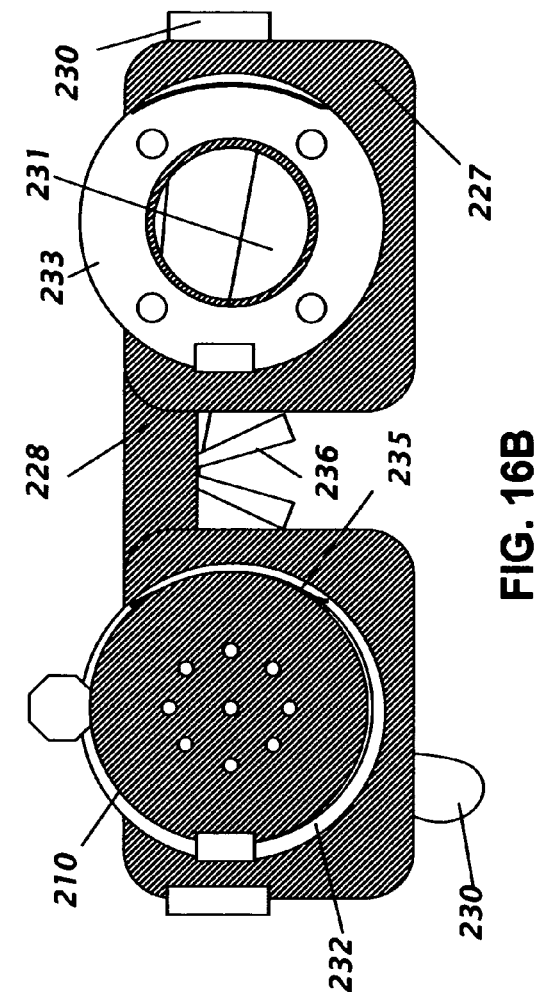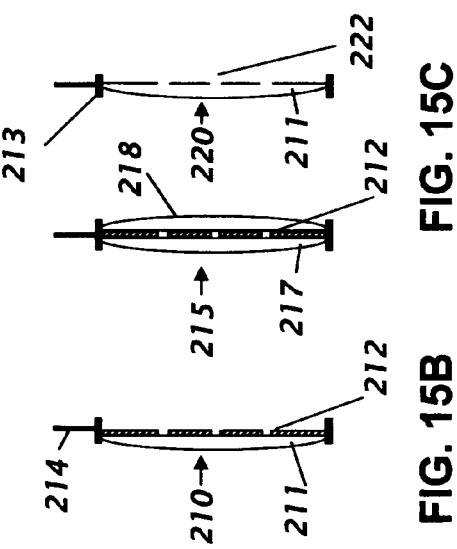

HAND-HELD DEVICE FOR CONTRAST AND MULTIFUNCTION VISION TESTING

CROSS REFERENCE TO RELATED APPLICATIONS

Not Applicable

STATEMENT REGARDING FEDERALLY SPONSORED RESEARCH OR DEVELOPMENT

Not Applicable

DESCRIPTION OF ATTACHED APPENDIX

Not Applicable

BACKGROUND OF THE INVENTION

This invention relates generally to the field of vision testing and more specifically to testing contrast sensitivity and multiple visual functions with a portable testing device and accessories.

Testing the functional capacity of the macula requires multiple measurements, for example, visual acuity, potential acuity, contrast sensitivity, glare impairment, vision distortion, color vision, and low vision. Unfortunately most patients do not receive this battery of test because many examiners do not have the needed equipment due to cost, space requirements for non-portable instruments, and the time required for testing with multiple devices.

Many contrast sensitivity tests are available and are used to measure the loss of contrast in patients with ocular diseases, such as, cataract and macular diseases. Arrays of symbols of varying size and varying contrast or sine wave patterns of varying frequencies and varying contrast are presented to a subject and the subject discerns the images until the image becomes to faint to decipher. The illumination level affects contrast sensitivity and brightness is a parameter requiring specification. Some commercially available devices for measuring contrast sensitivity are costly computer programs, such as, Medmont AT-20, Medmont International Pty. Ltd., Vermont, Australia and Mentor B-VAT II, Mentor Corp., Santa Barbara, Calif.; illuminated vision charts, such as, wall or stand mounted AC powered CSV-1000, Vector Vision, Greenville Ohio; and hand-held vision charts such as the externally illuminated Mars Letters Charts, Mars Perceptrix, Corp., Chappaqua, N.Y. There is currently no contrast sensitivity chart that is hand-held and internally illuminated. Internal illumination has the advantage of even light distribution and eliminating the influence of aberrant ambient light.

Glare testing currently involves the patient holding the Mentor BAT brightness acuity tester, Mentor Corp., Santa Barbara, Calif., and viewing a distance vision chart which required a examination lane with a projector and wall screen or the CSV-1000HGT (Halogen Glare Test) Vector Vision, Greenville Ohio that is mounted on a stand or wall and requires AC powered.

Color vision tests require a computer program or test plated viewed under special lamp that give the correct characters of the light.

Low vision testing requires magnifiers, special bright illuminating lamps, and a variety of vision testing charts.

The Retinal Acuity Meter or RAM® manufactured by AMA Optics, Inc. has helped to improve patient care by implementing a hand-held tester that is fast, easy and inexpensive, but it is limited to a single test, the potential vision test.

My invention of an internally illuminated and hand-held vision testing device that presents a battery of eye tests is time saving and overcomes many problems facing clinicians, such as, inefficient testing methods, costly investment in multiple instruments, large space requirements for non-portable instruments, and difficulties of controlling extraneous ambient light for test relying on externally illuminated. The simplicity of my time saving testing invention would likely encourage clinicians to perform more in depth testing and this could lead to improved health care.

BRIEF SUMMARY OF THE INVENTION

In accordance with a preferred embodiment of the invention, there is disclosed a contrast sensitivity testing device for measuring vision in humans comprising a hand-held instrument, a light source for illuminating a display window, a vision chart consisting of symbols of varying contrast and size, means of housing and providing optical elements for focusing at the designated testing distances, and means of gauging the designated testing distances, whereby a portable diagnostic instrument is provide for testing contrast sensitivity at near under controlled uniform lighting provide by internal illumination.

In accordance with a preferred embodiment of the invention, there is disclosed a multipurpose vision testing device for measuring in humans a variety of visual functions that include visual acuity, contrast sensitivity, potential vision, low vision, color vision, visual distortion or metamorphopsia, and glare testing. The invention is a compact hand-held instrument consisting of a light source for illuminating a display window, a vision chart having symbol types for testing at least one visual function, means of changing vision charts, an attachment for glare testing, means of housing and providing optical elements for focusing at the designated testing distances, and means of gauging the designated testing distances.

In accordance with a preferred embodiment of the invention, there is disclosed a multipurpose clip that fits over eyeglasses composed of an optical pinhole disc with one or more openings for sighting a visual target, an optical lens suspended in front of the optical pinhole disc by a hinge that swings the optical lens in and out of the line of sight, and means of occluding vision, whereby my clip improves utility by adding occlusion to the prior art pinhole and lens clip.

In accordance with a preferred embodiment of the invention, there is disclosed a device for correcting vision that fits into testing frames that consists of lenticular optics, an optical pinhole, and means of combining lenticular optics and the optical pinhole, whereby testing efficiency is improved by combining two steps into one step.

In accordance with a preferred embodiment of the invention, there is disclosed a pinhole-lens having an optically clear pinhole size void that is marginated by a light blocking ring. The pinhole-lens provides a panoramic view so that the subject can select the target for sighting through the pinhole.

In accordance with a preferred embodiment of the invention, there is disclosed a testing frame that fits over eyeglasses and accommodates optical pinhole, optical lens, and occluder for expediting testing with the vision testing device.

Other objects and advantages of the present invention will become apparent from the following descriptions, taken in connection with the accompanying drawings, wherein, by way of illustration and example, embodiments of the present invention are disclosed.

BRIEF DESCRIPTION OF THE DRAWINGS

The drawings constitute a part of this specification and include exemplary embodiments to the invention, which may be embodied in various forms. It is to be understood that in some instances various aspects of the invention may be shown exaggerated or enlarged to facilitate an understanding of the invention.

FIG. 2A is my contrast sensitivity vision chart on transparent film.

FIG. 2B is my color vision test chart on transparent film.

FIG. 2C is my vision chart with symbols of several test types.

FIG. 2D is my combined high contrast and graded contrast vision chart on transparent film.

FIG. 4A is perspective view of the vision chart holder showing laser triangulation.

FIG. 4B is perspective view of the vision chart holder showing laser triangulation with converging prism attached.

FIG. 5A is perspective view of the vision chart holder in the rigid testing support.

FIG. 5B is perspective view of the vision chart holder in the adjustable rigid testing support.

FIG. 6A is rear view of the hinged vision chart holder.

FIG. 6B is left side view of the hinged vision chart holder.

FIG. 6C is right side view of the hinged vision chart holder.

FIG. 6D is top view of the hinged vision chart holder.

FIG. 6E is perspective view of the hinged vision chart holder with hinge open.

FIG. 9A is perspective view of the glare inducing attachment and vision chart holder.

FIG. 9B is perspective view of the enclosed glare inducing attachment and the vision chart holder.

FIG. 10A is my single-piece tester with indirect imaging using mirrors as seen through the outer enclosure members.

FIG. 10B is my single-piece tester with the vision chart housing pulled out of the enclosure.

FIG. 11A is my single-piece tester with direct imaging as seen through the outer enclosure members.

FIG. 11B is the optical diagram of single-piece tester with indirect imaging using mirrors.

FIG. 11C is the optical diagram of single-piece tester with direct imaging.

FIG. 12 is my panoramic pinhole-lens in frontal view.

FIG. 13A are eyeglasses with a pinhole lens clip attached to each lens and the magnetic occluder is attached to the clip over the left eyeglass lens.

FIG. 13B is the magnetic occluder attached to the ferrous pinhole disc in frontal view.

FIG. 13C is the magnetic occluder attached to the ferrous pinhole disc in cross section view.

FIG. 13D is pinhole and lens clip with the fastening occluder attached in frontal view.

FIG. 13E is pinhole and lens clip with the fastening occluder attached in cross section view.

FIG. 14A is pinhole and lens clip with the vertical moving second pinhole disc with pinholes open in frontal view.

FIG. 14B is pinhole and lens clip with the vertical moving second pinhole disc with pinholes open in cross section.

FIG. 14C is pinhole and lens clip with the vertical moving pinhole disc with pinholes closed in frontal view.

FIG. 14D is pinhole and lens clip with the vertical moving pinhole disc with pinholes closed in cross section view.

FIG. 14E is pinhole and lens clip with the pivoting second pinhole disc with pinholes open in frontal view.

FIG. 14F is pinhole and lens clip with the pivoting second pinhole disc with pinholes open in cross section view.

FIG. 14G is pinhole and lens clip with the pivoting second pinhole disc with pinholes closed and with lens occluder attached in frontal view.

FIG. 14H is pinhole and lens clip with the pivoting second pinhole disc with pinholes closed and with lens occluder attached in cross section view.

FIG. 15A is my lenticular pinhole disc for use in testing frame in frontal view.

FIG. 15B is my lenticular pinhole disc for use in testing frame in cross section view FIG. 15C are two embodiments of my lenticular pinhole for testing frame in cross section view.

FIG. 16A is my testing frame in side view.

FIG. 16B is my testing frame in frontal view.

DETAILED DESCRIPTION OF THE PREFERRED EMBODIMENTS

Detailed descriptions of the preferred embodiment are provided herein. It is to be understood, however, that the present invention may be embodied in various forms. Therefore, specific details disclosed herein are not to be interpreted as limiting, but rather as a basis for the claims and as a representative basis for teaching one skilled in the art to employ the present invention in virtually any appropriate detailed invention, structure or manner.

Description, FIG. 1, Prior Art

Figure 1B:
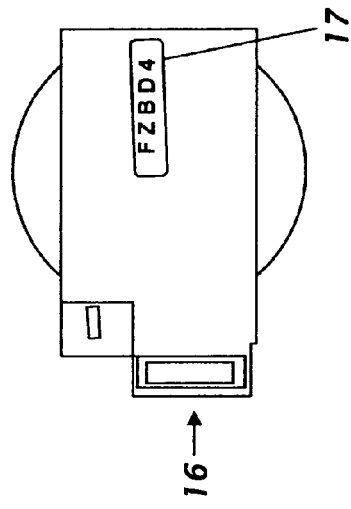
FIG. 1B shows prior art consisting of a frontal view of the Retinal Acuity Meter.
Figure 1A:
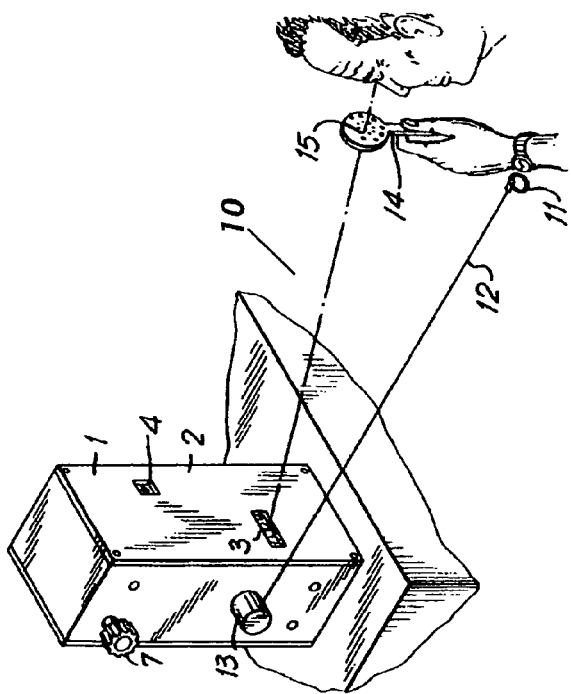
FIG. 1A shows prior art consisting of a perspective view of Device for Testing Vision Potential.
Figure 1C:
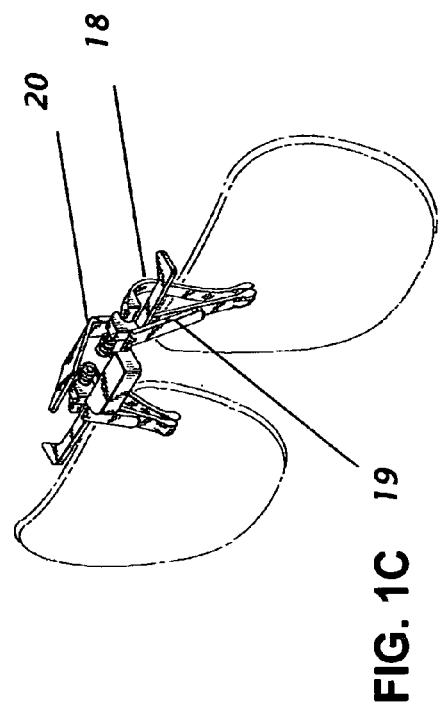
FIG. 1C shows prior art consisting of a perspective view of Clip for Clip-on Sunglasses.

In FIG. 1A is illustrated the DEVICE FOR TESTING VISION POTENTIAL of Hofeldt, U.S. Pat. No. 5,398,085, showing enclosure 1, front surface 2, window 3 for displaying symbols, window 4 for indexing the position of the chart, knob 7 for changing the images appearing in windows 3 and 4, ring 11 connecting to measuring string 12 which recoils into retractor 13, line of sight 10 of the subject viewing display window 3 which measuring 14 to 16 inches and passes through pinhole perforation 15, in pinhole disc 14. In FIG. 1B is the illustrated the hand-held internally illuminated RETINAL ACUITY METER 16 manufactured by AMA Optics, Inc. Miami Beach, Fla. showing window 17 displaying a line of high contrast symbols for measuring potential vision. In FIG. 1C is illustrated CLIP FOR CLIP-ON SUNGLASSES of Friedman with U.S. patent Des. 350,359 showing body of clip 20 with arm 18 for clamping on to eyeglasses, arm 19 for attaching optical lens.

My invention is a portable vision tester for humans measuring one or a battery of visual functions at near distance for diagnostic purpose. The invention has accessories that broaden the variety of vision tests, means of presenting and illumination a vision chart under controlled internal lighting conditions, means of gauging the testing distance, means of optical focusing and occluding, and means of holding optical focusing elements. My compact multipurpose vision testing device makes it possible to efficiently measure a plurality of visual functions in a variety of clinical settings. The following figures separate my invention into components for teaching the operation of the invention and illustrating how the components are critically interdependent.

A key element of my invention is the vision chart with symbols printed or photographed onto a background material. Examples of vision charts of my invention for measuring a variety of visual functions are illustrated in FIGS. 2A-2D. Single parameter vision charts are seen in FIGS. 2A and 2B. Contrast sensitivity vision chart 20 seen in FIG. 2A has 17 lines of symbols of varying contrast and size for viewing sequentially in an illuminated display window. In FIG. 2B is color vision chart 21 having nine color vision symbols and color plate 22 is one such plate for testing color vision. In FIG. 2C vision chart 23 combines color symbols, for instance plate 22, a grid symbol 24 for measuring metamorphosis or visual distortion, and high contrast symbols for instance letter 25 for measuring visual acuity, retinal acuity or potential vision, and for glare testing. Vision chart 26 in FIG. 2D is made up of high contrast letter for instance letter 27 and low contrast letters for example letter 28 of 20% contrast and letter 29 of 10% contrast.

Figure 3C:
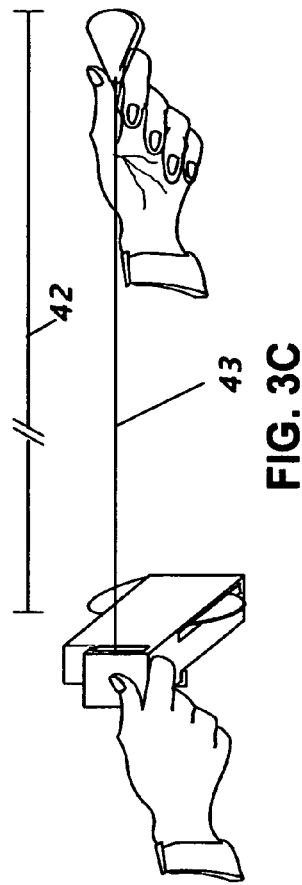
FIG. 3C is perspective view of the vision chart holder with single retractor.
Figure 3D:
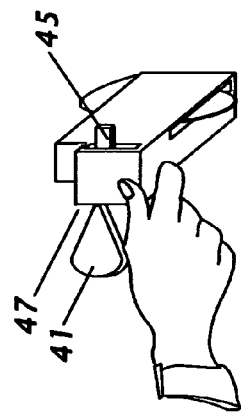
FIG. 3D is perspective view of the vision chart holder with single retractor showing the pull.
Figure 3E:
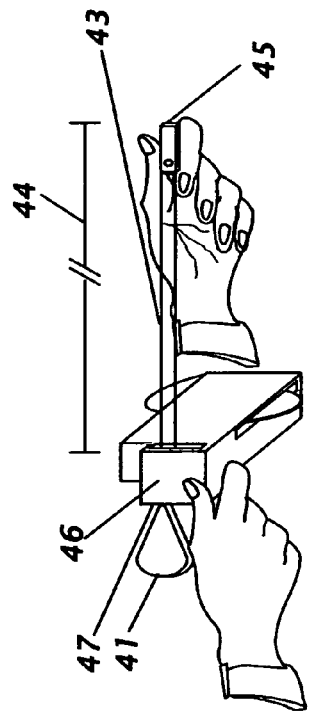
FIG. 3E is perspective view of the vision chart holder with single retractor showing the pull extended.
Figure 3A:
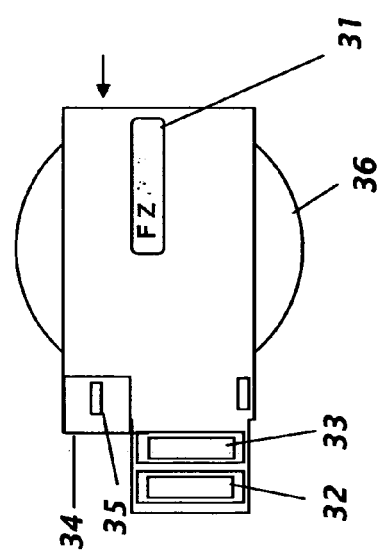
FIG. 3A is a frontal view of the vision chart holder with dual retractor.
Figure 3B:
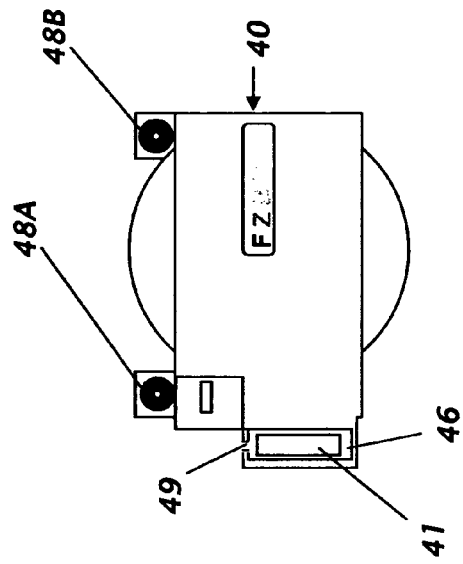
FIG. 3B is a frontal view of the vision chart holder with lasers and single retractor.
Figure 7B:
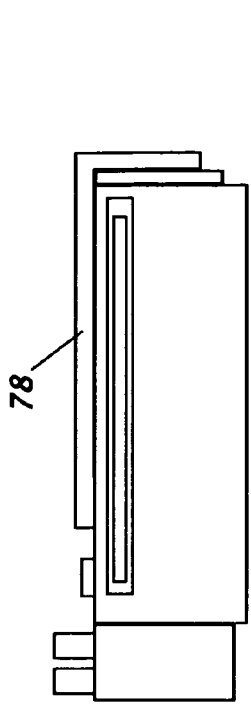
FIG. 7B is bottom view of the vision chart holder with color correcting filter attached.
Figure 7D:
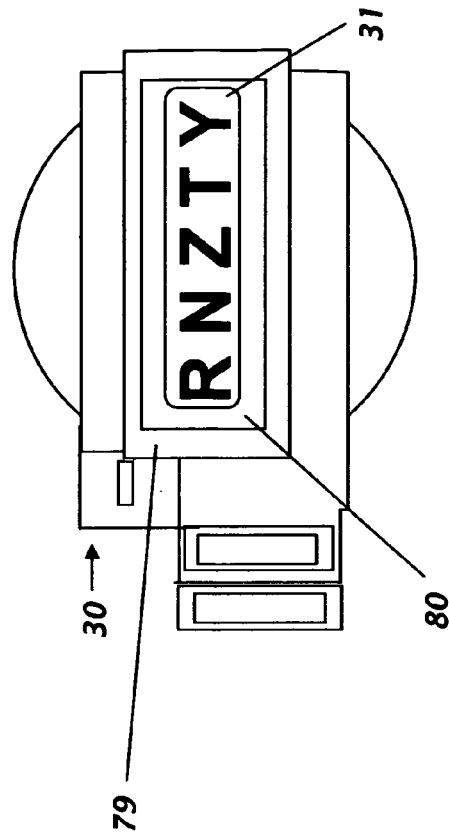
FIG. 7D is frontal view of the vision chart holder with magnifier attached.
Figure 7A:
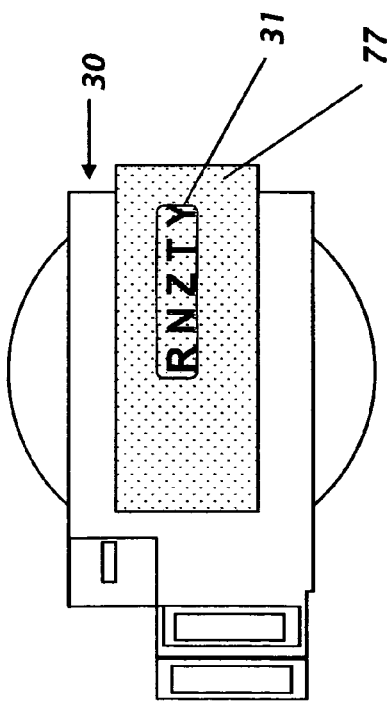
FIG. 7A is frontal view of the vision chart holder with light attenuating filter attached.
Figure 7C:
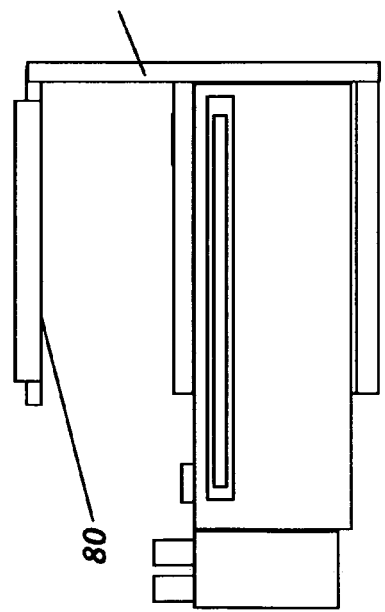
FIG. 7C is side view of the vision chart holder with magnifier attached.

One embodiment of my vision chart holder is tester 30 consisting of enclosure 34, on/off light switch 35, dual retractors 32 and 33, and light diffusion disc 36 where upon is mounted one of my vision charts having symbols of one or more test types for viewing in display window 31. In FIG. 3A are representative vision chart symbols of my contrast sensitivity test type in display window 31 of my vision chart holder 30.

Several of my test types are designed to be viewed at two different distances and this requires focusing facility and length gauging for two distances, distance 42 and shorter distance 44. The lenses as illustrated in FIG. 13E provide for focusing at two distances, distance 42 with lens 182 and distance 44 with lens 182 and lens 183 joined together. The resulting focal length is the sum of the focal lengths of lens 182 and lens 183. I have provided four means of measuring more than one testing distance. The first means for gauging two distances is with cords spooled onto recoiling retractors as illustrated in FIG. 3A by the cord of retractor 32 gauging distance 42 and the cord of retractor 33 gauging distance 44. The second means for gauging two distances is with single cord retractor 41 as illustrated in FIGS. 3B-3E. In detail, single cord retractor 41 gauges distance 42 when the cord 43 is fully extended as in FIG. 3C and gauges distance 44 when cord 43 is looped through pull 45 and pull 45 is fully extended as in FIG. 3E. To use pull 45, retractor 41 resting on top of pull 45 in receptacle 46 is transferred and attached to the rear surface 47 by passing cord 43 through slot 49 which shifts pull 45 out of the base of receptacle 46 and exposes pull 45 as shown in FIG. 3D. Pull 45 can then be grasped to extend cord 43 to gauge distance 44 as seen in FIG. 3E. The third means for gauging two distances is by using low energy lasers for triangulation as seen in FIGS. 4A and 4B with laser 48A and 48B. Lasers 48A and 48B are mounted on the body of vision chart holder 40 and are aligned so that laser beams 50A and 50B converge to intersect at point 51 to gauge distance 42. Second testing distance 44 is gauged by placing converging prism 52 to deviate the laser beam 50B so that beam 50A and 50B intersect at a shorter testing distance as illustrated in FIG. 4B. The fourth means for gauging two distances is with rigid testing support 60 having extension 39 for measuring distance 44 as seen in FIG. 5A. Receptacle 62 holds vision chart holder 40 while rigid testing support 60 abuts against the forehead of the subject being tested. Longer distance 42 can be gauged with recoiling retractor 41. Capable of measuring multiple distances is adjustable rigid testing support 63 illustrated in FIG. 5B having slots 64A, 64B, 65A, and 65B to accommodate sliding guide fasteners 66A, 66B, 66C, and 66D so that plate 67 can be repositioned in relation to plate 68 to gauge a testing distance of the desired length as indexed by ruler 69. An added benefit of rigid testing supports 60 and 63 is the stability of the testing distance which is particularly important when testing at short distances where movement of a fraction of an inch can significantly affect the visual angle of the perceived image.

Advance to FIGS. 6A-6E to see an embodiment of my invention providing means of exchanging vision charts where the vision chart holder 70 has hinge 71 that opens body 72 and has latch 73 to maintain body 72 closed. As illustrated in perspective drawing in FIG. 6E, releasing latch 73 opens hinge 71 and exposes the illuminating source, light bulb 74, and diffusion disc 36. Diffusion disc 36 with an attached vision chart can be removed by releasing snap 75 and replaced with a different diffusion disc and vision chart which increases the functionality of the invention.

Accessories that expand the variety of tests of my vision testing invention are seen in FIGS. 7, 8, and 9. In FIG. 7A is frontal view of vision chart holder 30 showing attachment 77, a neutral density filter for attenuating the brightness level, and in FIG. 7B is vision chart holder 30 with color correcting filter attachment 78 for altering characteristics of the radiating form display window 31 as viewed from the bottom of vision chart holder 30. In FIG. 7C is a bottom view and in FIG. 7D is a frontal view of vision chart holder 30 showing magnifying lens attachment 79. Illustrated in FIG. 7D in display window 31 are magnified letters as viewed through magnifying lens 80. Magnifying lenses can be useful to enlarge images for low vision, color vision, and visual distortion testing.

Figure 8B:
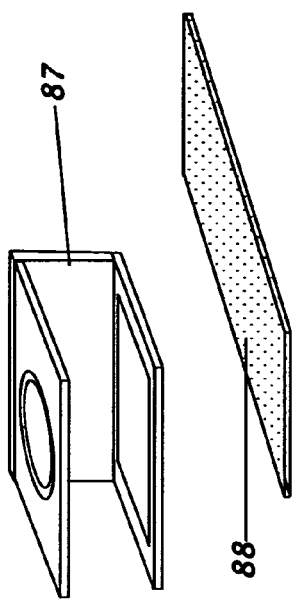
FIG. 8B are perspective views of the magnifier and light filter.
Figure 8D:
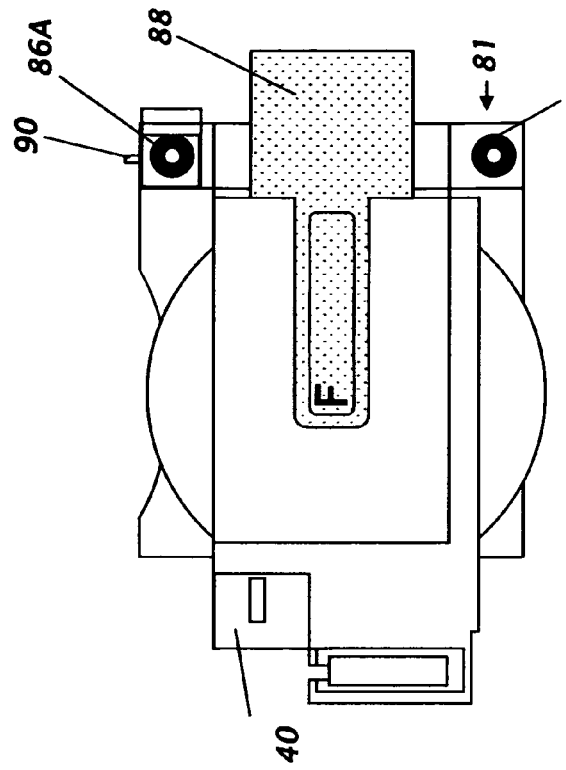
FIG. 8D is frontal view of the vision chart holder in the accessory module with filter attached.
Figure 8A:
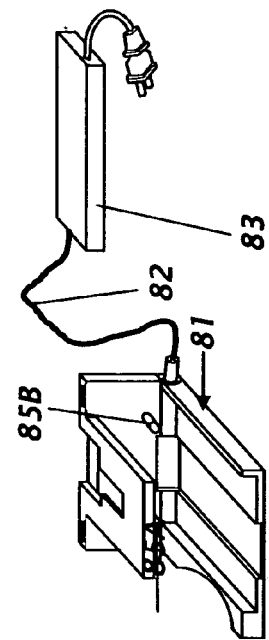
FIG. 8A is perspective view of the accessory module with a battery charger attached.
Figure 8C:
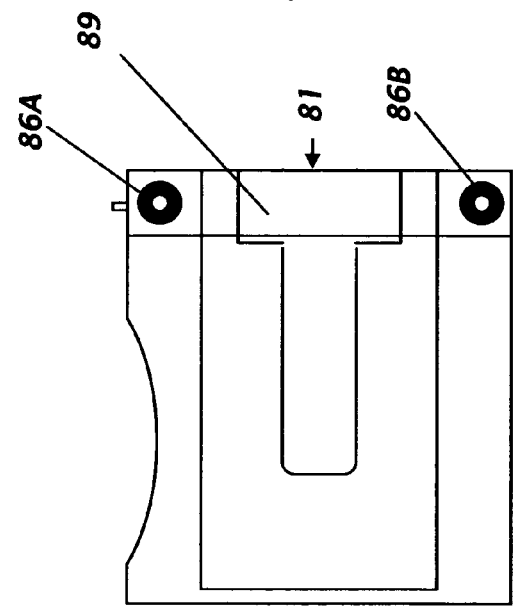
FIG. 8C is frontal view of the accessory module.

A module for my vision testing invention that combines with interchangeable accessories is seen in FIGS. 8A-8D. In FIG. 8A is a perspective view of modular docking cradle 81 showing electrical cord 82 connecting between docking cradle 81 and battery charger 83. For recharging, electrical current passes from battery charger 83 through electrical terminals 85A and 85B to vision chart holder 40. Besides serving as a recharging stand, docking cradle 81 also provides support for accessories such as magnifying loupe 87 for testing low vision, color vision and visual distortion, and light filter 88 for altering the light radiating from display window 31 shown in FIG. 8B and in FIG. 8D. In addition docking cradle 81 provides means of gauging testing distance by incorporating triangulating lasers 86A and 86B into the body of the module 81 as seen in FIG. 8C. In FIG. 8D is shown vision chart holder 40 fitted into docking cradle 81 with light filter 88 inserted into slot 89. Switch 90 actives lasers 86A and 86B.

Another important accessory of my vision testing invention for evaluating cataract patients is glare inducing attachment 100 as shown in FIG. 9A with viewing end 101 abutting against the forehead of the subject while the subject views vision chart holder 40 at the end opposite the viewing end. Chart holder 40 is held in receptacle 102 that is positioned perpendicular to the line of sight of the subject. The four sided frame of glare inducing attachment 100 consists of top plate 104 and bottom plate 103, vertical supports 105 and 106, and instrument receptacle 102. Glare lights pointing towards the eyes of the subject as illustrated by glare light 106 and brightness control 107 is mounted on plate 103. The electric power supply of vision chart holder 40 supplies the power to the glare lights through power outlet 109 and connector 108. In FIG. 9B all sides of glare inducing attachment 100 are covered and on side 110 is mounted battery compartment 111 that powers the glare lights through connector 112. Switch 113 changes the light intensity of all the glare lights.

A further embodiment of my vision testing invention is the single-piece tester 120 having all elements enclosed as illustrated in FIGS. 10A and 10B with enclosure 121 housing exchangeable eyepiece 122 containing a combination of optical pinhole 123, optical lens 124, and light filters 125. As seen through the outer enclosure members in drawings FIGS. 10A and 10B are right viewing chamber 126; left viewing chamber 127; first mirror 128; second mirror 129; partition 130; window in partition 131; display window 132 in light blocking barrier 133; vision chart assembly 134 containing vision chart 135, diffuser 136, cone reflector 137 and lamp 138; battery housing 139; light switch 140; indices 141; and index mark 142. Symbols of chart 135 are rotated for viewing in display window 132 by turning battery housing 139 which in turn rotates chart housing 134. Unfastening retaining ring 143 as seen in FIG. 10B allows removal of vision chart assembly 134 for exchanging vision chart 135. Switch housing 143 hold switches such as switch 144 for controlling the intensity of the glare lights mounted in right viewing chamber 126 as depicted by glare light 150 in FIG. 11A. In FIG. 11B is the optical diagram of indirect imaging in the single-piece tester 120 showing optical pinhole 123, optical lens 124, light filter 125, first mirror 128 and second mirror 129 to reflect the images, and display window 132 displaying symbols of chart 135. Another embodiment is single-piece tester 160 that has direct imaging as illustrated in the see though drawing of FIG. 11A and optical diagram of FIG. 11C. Sighting is from eyepiece 122 to upright chart symbols 162 in display window 161 through single viewing chamber 163.

The optical pinhole, as we know it, is an optically clear perforation in a light blocking material which improves focusing by restricting the light to a small bundle of rays that are relatively independent of the laws of refraction, but the improved focusing is at the expense of tunnel vision due to the restricted field of view. Part of my vision testing invention is my panoramic pinhole-lens that retains the benefit of a small bundle of rays and adds the benefit of an unrestricted field of view. One embodiment of my panoramic pinhole-lens is disc 165 in FIG. 12 showing pinhole ring 166 that forms a margin of light blocking material around a round and optically clear void. Pinhole ring 166 is surrounded by a transparent material 167 that allows a panoramic view for a subject viewing through disc 165. Another embodiment of my panoramic pinhole-lens is disc 168 where pinhole ring 169 is surrounded by material 170 that partially blocks light. Yet another embodiment of my panoramic pinhole-lens is disc 171 with material 172 surrounding pinhole ring 173 that blends from complete light blockage to partial light blockage. Within pinhole rings 166, 169 and 173 the space could be a perforation or an optical clear material that may have light refracting and laser light blocking properties. The material 167, 170 and 172 may have light refracting and laser light blocking properties. By expanding the field of view, my panoramic pinhole-lens is particularly useful in single-piece testers 120 and 160 for assisting the subject in selecting the visual target since the fixed angle between the optical pinhole 123 and the display windows 132 or 161 exaggerates the tunnel vision effect because the pinhole cannot be freely positioned for sighting as is possible when the optical pinhole is attached to eyeglasses.

For making focusing and occluding fast and easy for the clinician, my invention combines vision correcting and occluding elements in a clip that fits over the lens of eyeglasses as illustrated by clip 180 in FIGS. 13A-13E. In FIG. 13A is illustrated clip 180 made up of body 20 as specified by U.S. patent Des. 350,359, metallic pinhole disc 181 and optical lens 182. Arm 19 of body 20 raises and lowers and swings optical lens 182 in and out of the line of sight. By using two clips, one over the right eye and one over the left eye as seen in FIG. 13A, alternate eyes can be tested by simply moving magnetic occluder 184 from one side to the other. Magnetic occluder 184 attaches by magnetism to ferrous containing pinhole disc 181 and occludes all pinhole openings as illustrated in FIG. 13B by blocking pinholes 185A and 185B. Alternatively, disc 184 could be a light weight material and held in position by friction between lens 182 in the lowered position and the apposing pinhole disc 181. In FIG. 13C occluder 186 is non-magnetic and attaches to pinhole disc 181 by fastener 187 fitting over pinhole disc 181 and held in position by friction. Another embodiment for combining vision correcting and occluding device is seen in FIG. 14A where pinhole disc 188 and moveable secondary pinhole disc 189 have pinhole openings in the same pattern and pinhole disc 188 is attached to second pinhole disc 189 by screws 190 A and 190B and held in position by pin 191. When second disc 189 is grasped by handle 192 and lowered so that pin 191 moves from opening 193 to opening 194, second disc 189 occludes all pinholes in pinhole disc 188 as illustrated by blocked pinhole 195A and 195B in FIG. 14D. Another embodiment is seen in FIGS. 14E-14H, where second disc 196 and pinhole disc 197 have pinhole openings in the same pattern and where second disc 196 attached to pinhole disc 197 by screw 198 so that when second disc 196 pivots in regards to pinhole disc 197, pin 199 changes from hole 200 to hole 201 and all pinholes are occluded as illustrated by holes 203A and 203B. Also illustrated in FIGS. 14G and 14H is lens occluder 240 that attaches to lens 182 by a fastener held in place by friction. When occluder 240 and lens 182 are lowered into the line of sight, the pinholes are blocked.

Currently, trial frames are used to completely correct the refractive error of the subject and are not designed to fit over eyeglasses. My invention includes a testing frame that fits over eyeglasses to accommodate an optical pinhole and only sufficient optical correction for focusing at near because my invention utilizes the refractive power of the eyeglasses to correct the refractive error for distance. My preferred embodiment for holding vision correcting members when testing with vision chart holders 30 and 40 is my testing frame 225 shown in FIGS. 16A and 16B that adequately fit over eyeglasses. Light blocking shields 226 and 227 attach to cross support 228 which connect to foldable temples 229 and 230 and nosepiece 236. Shields 226 and 227 have a central optically clear zone 231 aligning with the visual axis of the subject and clear zone 231 may have optically refractive power and filter properties to block laser radiation. Affixed to shields 226 and 227 are retainers 232 and 233 that have indentations such as groove 234 and means to accept and grip optical correcting elements such as spring 235.

To make vision testing with testing frame 225 or with commercial trial frames more efficient, I have combined the optical pinhole and the corrective lens into a single device, a lenticular pinhole disc. In FIG. 15A is a frontal view of my lenticular pinhole disc 210 that fits into testing frame 225. In FIG. 15B is cross section of lenticular pinhole 210 where optical lens 211 and optical pinhole disc 212 are held in apposition by circumferential ring 213 that is equipped with grasping handle 214. Another embodiment is lenticular pinhole 215 that sandwiches pinhole disc 212 between optical lens 217 and 218 which are held together by ring 213. By dividing the lens power into two lenses, a lens covers each side of pinhole disc 212 and prevents debris from collecting in the openings and blurring the view. Yet another embodiment is lenticular pinhole 220 consisting of optical lens 221, thin layer light blocking film 222 that is produced by a photographic, printing, or etching process, and retaining ring 213. Lenticular pinhole 220 has the advantages of reduced thickness and the absence of pinhole recesses that could collection debris.

While the invention has been described in connection with a preferred embodiment, it is not intended to limit the scope of the invention to the particular form set forth, but on the contrary, it is intended to cover such alternatives, modifications, and equivalents as may be included within the spirit and scope of the invention as defined by the appended claims.

What is claimed is:

1. A hand-held contrast sensitivity testing device for measuring vision in humans, comprising:
   a) a vision chart holder having an internal illuminating light source;
   b) means of displaying a single lines of symbols of a multiple line chart sequentially in a display window;
   c) a vision chart consisting of multiple lines of symbols of varying contrast and size;
   d) means of housing and providing optical elements for focusing at near testing distances; and
   e) means of gauging said testing distances,
   whereby a portable instrument is provided for testing contrast sensitivity with controlled internal lighting.

2. A hand-held multipurpose vision testing device for humans, comprising:
   a) a vision chart holder having an internal illuminating light source;
   b) means of displaying a single lines of symbols of a multiple line chart sequentially in a display window;
   c) means of presenting multiple lines of symbols for testing a plurality of visual functions;
   d) means of housing and providing optical elements for focusing at near testing distances, with said optical elements including a transparent lens having one or more light blocking areas and within, each said area is a round optically clear pinhole aperture; and
   e) means of gauging said testing distances,
   whereby a portable diagnostic instrument is provided for testing a battery of vision functions with controlled internal lighting.

3. The device of claim 2 wherein said plurality of vision test types includes visual acuity, potential vision, color vision, contrast sensitivity, low vision, glare testing, and vision distortion.

4. The device of claim 2 wherein said means of presenting symbols for testing a plurality of visual functions is a vision chart having symbols of more than one test type.

5. The device of claim 2 wherein said means of presenting a plurality of visual functions are exchangeable vision charts made up of symbols of at least one test type.

6. The device of claim 2 where a switch changes the intensity of said light source.

7. The device of claim 2 where a light filter attaches over said display window and changes the characteristics of the radiating light.

8. The device of claim 2 wherein said means for housing and providing optical focusing elements is a testing frame, comprising:
   a) a frame of sufficient size to fit over eyeglasses;
   b) right and left occluding shields made of a light blocking material that have a central clear optical zone aligning with the visual axis of the subject; and
   c) right and left retainers affixed to said light blocking shields that accept and grips optical lenses, an optical pinhole, filters and an occluder.

9. The device of 8 wherein said clear optical zone is made of a material that blocks laser light and may have optical refractive power.

10. The device of claim 2 wherein said means of gauging testing distances comprise:
    a) a first cord attached to said vision chart holder where the length of said first cord gauges distance A when said first cord is fully extended;
    b) a second cord attached to said vision chart holder where the length of said second cord gauges distance B when said second cord is fully extended; and
    c) retractors that recoil and spool said first and second cords,
    whereby one instrument can gauged two testing distances.

11. The device of claim 2 wherein said means of gauging testing distances comprise:
    a) a recoiling retractor spooling a cord with said cord attaching to said vision chart holder so that distance A is gauged when said retractor is fully extended and
    b) said cord gauges second distance B when said cord and said retractor are attached to said hand-held vision chart holder and said cord passes through a pull, and said pull is fully extended,
    whereby two testing distances are gauged by a one cord.

12. The device of claim 2 wherein said means for gauging the testing distance is a rigid testing support, comprising:
    a) a rigid extension that abuts against the forehead of the subject and gauges the distance from the eyes of said subject to said display window of said vision chart holder and
    b) a receptacle for holding said vision chart holder at the gauged testing distance.

13. The device of claim 2 wherein said means for gauging the testing distance is by laser light triangulation, comprising:
    a) a first and a second low energy laser;
    b) power supply for said lasers; and
    c) mounting said lasers on the body of said vision chart holder and aligning said lasers such that the beams of the said lasers converge and intersect to gauge distance A, converge and intersect to gauge distance B when converging prism b deviates the path of one beam of said lasers, and converge and intersect to gauge distance C when converging prism c deviates the path of one beam of said lasers, whereby more than one testing distances can be gauged with one instrument.

14. The device of claim 2 having a magnifying lens attachment to enlarge the size of the symbols in said display window while viewing through said magnifying lens.

15. The device of claim 2 having a modular docking cradle for providing housing for said triangulating lasers; for providing a stand for said vision chart holder during battery recharging; and for providing electrical connection from the power supply of said vision chart holder to a battery charger and to said lasers; and for providing support for accessories such as light filters and magnifying lenses that attach over said display window.

16. The device of claim 2 wherein is attached to a hand-held glare inducing device, comprising:
 a) a viewing frame of the length for near vision testing having four sides of which at least two of said four sides support glare lights and lighting controls with said glare lights aligned such that beams from said glare lights point towards the eyes of the subject;
 b) a viewing end of said viewing frame that abuts against the forehead of said subject for viewing said display window of said vision chart holder positioned at the opposite end of said viewing frame; and
 c) a receptacle to support said vision chart holder in such a position that said display window is in the line of sight of said subject.

17. The device of claim 2 wherein all elements are enclosed is a single-piece, comprising:
 a) an enclosure having an exchangeable eyepiece with said eyepiece housing a combination of optical lenses, an optical pinhole with said optical pinhole being a transparent lens having one or more light blocking areas and within each said area is a round optically clear pinhole aperture, and light filters for sighting said line of symbols;
 b) means of changing the brightness of the display window; and
 c) a removable vision chart housing for exchanging said vision chart with other vision charts having symbols of different test types.

18. The device of claim 17 where in the optical path has a mirror arrangement that reflects said line of letters for focusing through said eyepiece.

19. The device of claim 17 wherein glare lights for glare testing are mounted within said enclosure so that beams from said glare lights are pointing towards said eyepiece with said glare lights having lighting controls to change the light intensity.

* * * * *